United States Patent [19]

Rogers

[11] 4,021,500

[45] May 3, 1977

[54] OXIDATIVE DEHYDROGENATION SYSTEM

[75] Inventor: Ronald S. Rogers, Bartlesville, Okla.

[73] Assignee: Phillips Petroleum Company, Bartlesville, Okla.

[22] Filed: Sept. 13, 1972

[21] Appl. No.: 288,731

[52] U.S. Cl. .................................. 260/680 E
[51] Int. Cl.² ................................... C07C 5/48
[58] Field of Search ........................ 260/680 E

[56] References Cited

UNITED STATES PATENTS

| 3,557,238 | 1/1971 | Cunningham | 260/680 E |
| 3,646,239 | 2/1972 | Hutson et al. | 260/680 E |

Primary Examiner—Paul M. Coughlan, Jr.

[57] ABSTRACT

An improved oxidative dehydrogenation system recycles separated water from the system to a catalytic oxidation reactor at which location organic compounds in the separated water are converted to materials such as carbon dioxide, carbon monoxide and water vapor with the resultant treated water being recycled to a dehydrogenation catalytic reactor of the system.

4 Claims, 1 Drawing Figure

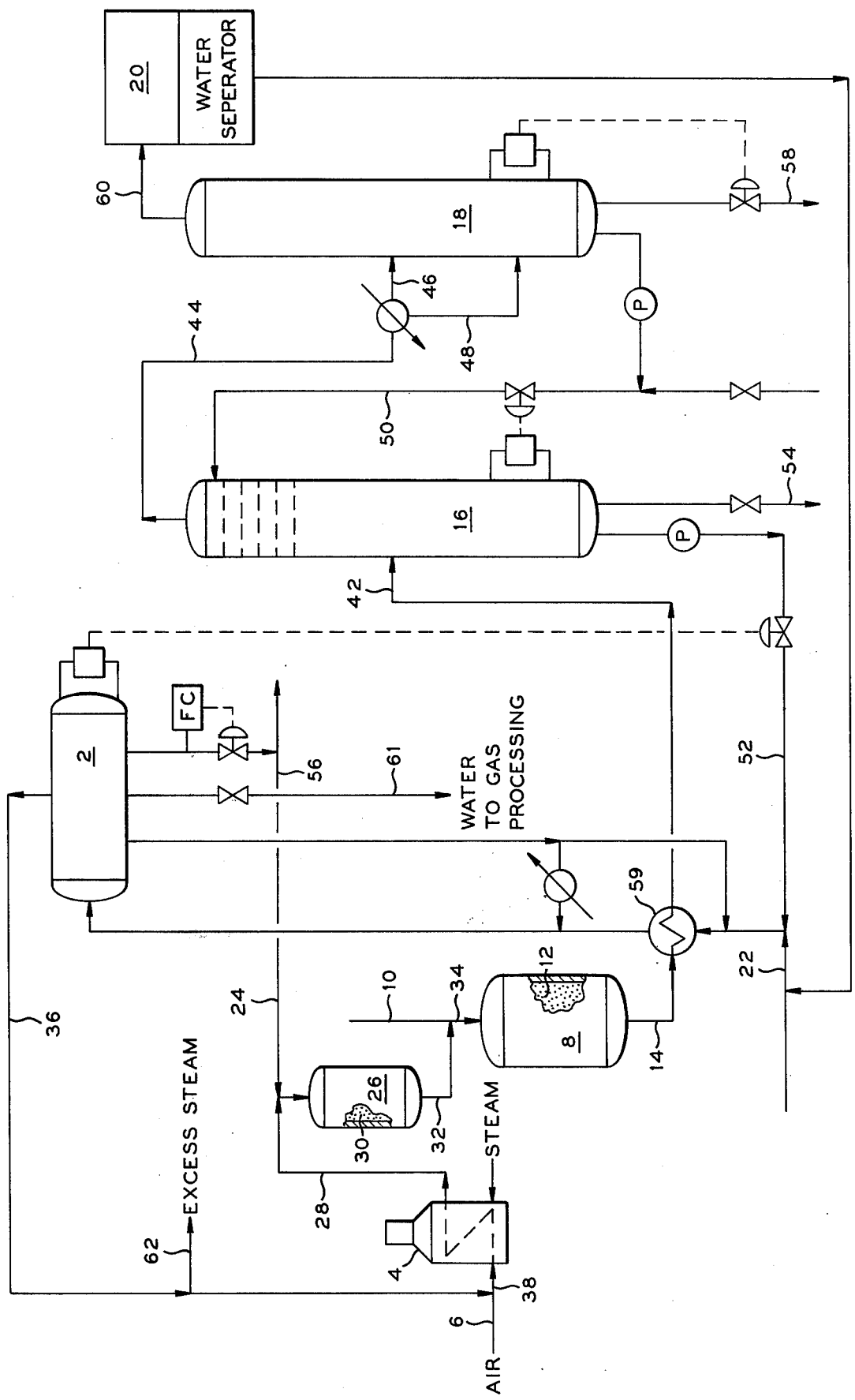

OXIDATIVE DEHYDROGENATION SYSTEM

In an oxidative dehydrogenation system utilized for oxygenating and dehydrogenating a hydrocarbon feed stream to form a resultant product from which water is separated, the separated water is generally sufficiently contaminated with hydrocarbons to cause said water to be undesirable for reuse in the process. This separated water has heretofore been disposed of which disposal has represented a relatively large expenditure of time, labor, and equipment owing to its volume and undesirable characteristics.

This invention therefore resides in an oxidative dehydrogenation system wherein separated water is recycled from the system to a catalytic oxygenation reactor at which location organic compounds in the separated water are converted to harmless materials such as carbon dioxide, water vapor and carbon monoxide with the resultant treated water being recycled to a dehydrogenation catalytic reactor of the system.

Other aspects, objects, and advantages of the present invention will become apparent from a study of the disclosure, the appended claims, and the drawing.

The drawing is a diagrammatic view of the oxidative dehydrogenation system having the improvement of this invention.

Referring to the drawing, a steam drum 2 is connected to a furnace 4 having an air stream 6 for mixing air and steam and heating said air and steam mixture to a preselected temperature.

A dehydrogenation reactor 8 having catalyst 12 therein receives the heated air-steam mixture from the furnace 4 and a hydrocarbon feed stream 10. In the reactor, the hydrocarbon feed steam contacts the catalyst 12 in the presence of air and steam and converts the hydrocarbons, for example from butene to butadiene. The effluent steam 14 from the dehydrogenation reactor 8 passes through other process equipment, such as for example a quench tower 16, a separator 18, and a gas processing apparatus 20 for further processing.

The effluent stream 14 discharging from the dehydrogenation reactor comprises water, dehydrogenated hydrocarbon, oxygenated hydrocarbon derivatives, and unconverted hydrocarbon.

At a locus downstream of the reactor 8, water is separated from the products comprising the effluent stream 14 and recycled via conduit 22 to the steam generator 59 and thence to steam drum 2.

In the process, excess water is received by the steam generator. This recycle water is passed from the steam drum via conduit 24 into an oxidation reactor 26 which is connected via conduit 28 to the furnace 4 for receiving the heated air-steam stream therefrom.

A catalyst 30 in the oxidation reactor 26 converts the organic compounds in the separated water from the steam drum into carbonaceous gas, such as carbon monoxide and/or carbon dioxide and into water vapor for example.

The effluent from the oxidation reaction 26 which comprises the treated water, generally as steam, is passed via conduit 32 into the dehydrogenation reactor 8.

It is preferred that conduit 32 be associated with the hydrocarbon feed stream 10 at a location upstream of the reactor 8 for mixing the hydrocarbon feed stream with the treated water effluent from the reactor 26 to form a resultant mixture for passing the resultant mixture into the dehydrogenation reactor 8 via a single conduit 34.

By utilizing the method and apparatus of this invention, a basic problem in oxidative dehydrogenation processes is the elimination of by-product oxygenated organic material. To do this the by-product organics of diverse and small quantities are being removed by water and this leads to the problem of the disposal of the contaminated water. This invention provides a process that eliminates all organics in the water and results in their conversion to carbon monoxide and carbon dioxide which can be disposed of to the air. The process is a continuous one and operates concurrently with the plant facilities.

The following is an example calculated material balance more fully describing an example process of this invention.

TABLE I

| Component | 10 | 36 | 38 | 28 | 6 | 34 | 14 | 42 | 44 | 46 | 48 |
|---|---|---|---|---|---|---|---|---|---|---|---|
| Nitrogen | | | 72,547 | 72,547 | 72.547 | 72,547 | 72,547 | 72,547 | 72,547 | 72,547 | |
| Carbon Monoxide | | | | | | | 10,096 | 10,096 | 10,096 | 10,096 | |
| Oxygen | | | 22,627 | 22,627 | 22,627 | 22,027 | 7,095 | 7,095 | 7,095 | 7,095 | |
| Methane | | | | | | | 46 | 46 | 46 | 46 | |
| Ethylene | | | | | | | 134 | 134 | 134 | 134 | |
| Ethane | | | | | | | 17 | 17 | 17 | 17 | |
| Carbon Dioxide | | | | | | | 3,326 | 3,326 | 3,326 | 3,326 | |
| Propylene | 304 | | | | | 304 | 967 | 967 | 967 | 967 | |
| Propane | 15 | | | | | 15 | 78 | 78 | 78 | 78 | |
| Isobutane | 670 | | | | | 670 | 670 | 670 | 670 | 670 | |
| Isobutylene | 45 | | | | | 45 | 11 | 11 | 11 | 11 | |
| Butene-1 | 10,695 | | | | | 10,695 | 1,971 | 1,971 | 1,971 | 1,971 | |
| Butadiene | 879 | | | | | 879 | 31,726 | 31,726 | 31,726 | 31,726 | |
| n-Butane | 590 | | | | | 590 | 590 | 590 | 590 | 590 | |
| Butene-2 trans | 21,317 | | | | | 21,317 | 7,071 | 7,071 | 7,071 | 7,071 | |
| Butene-2 cis | 16,382 | | | | | 16,382 | 4,521 | 4,521 | 4,521 | 4,521 | |
| Vinyl Acetylene | 147 | | | | | 147 | 145 | 145 | 145 | 145 | |
| $C_5^+$ | 17 | | | | | 17 | 17 | 17 | 17 | 17 | |
| Aldehyde and Acid | | 602 | 583 | 583 | | 23 | 768 | 768 | 752 | 38 | 714 |
| Water | | 433,024 | 433,024 | 419,603 | | 466,203 | 479,624 | 479,624 | 469,626 | 6,710 | 462,916 |
| Total | 51,062 | 433,626 | 528,781 | 615,360 | 94,574 | 612,398 | 612,421 | 612,421 | 602,410 | 138,779 | 463,630 |
| Temp., ° F. | 150 | 310 | 318 | 1,152 | 350 | 1,050 | 1,125 | 410 | 245 | 130 | 130 |
| Pressure, psia | 65 | 80 | 75 | 55 | 80 | 45 | 37 | 34 | 32 | 30 | 30 |

| Component | 50 | 52 | 54 | 56 | 60 | 58 | 60 | 62 | 22 | 61 | 32 |
|---|---|---|---|---|---|---|---|---|---|---|---|
| Nitrogen | | | | | | | 72,547 | | | | 72,547 |
| Carbon Monoxide | | | | | | | 10,096 | | | | 160 |
| Oxygen | | | | | | | 7,095 | | | | 22,027 |

TABLE I-continued

| | Stream Number - Pounds per Stream Hour | | | | | | | | | | |
|---|---|---|---|---|---|---|---|---|---|---|---|
| Methane | | | | | | | 46 | | | | |
| Ethylene | | | | | | | 134 | | | | |
| Ethane | | | | | | | 17 | | | | |
| Carbon Dioxide | | | | | | | 3,326 | | | | 1,000 |
| Propylene | | | | | | | 967 | | | | |
| Propane | | | | | | | 78 | | | | |
| Isobutane | | | | | | | 670 | | | | |
| Isobutylene | | | | | | | 11 | | | | |
| Butene-1 | | | | | | | 1,971 | | | | |
| Butadiene | | | | | | | 31,726 | | | | |
| n-Butane | | | | | | | 590 | | | | |
| Butene-2 trans | | | | | | | 7,071 | | | | |
| Butene-2 cis | | | | | | | 4,521 | | | | |
| Vinyl Acetylene | | | | | | | 145 | | | | |
| $C_5+$ | | | | | | | 17 | | | | |
| Aldehyde and Acid | 707 | 637 | 86 | 54 | | 7 | 38 | 19 | 600 | 200 | |
| Water | 458,316 | 412,484 | 55,830 | 46,600 | 45 | 4,600 | 6,710 | 13,421 | 334,000 | 334,000 | 466,203 |
| Total | 459,023 | 413,121 | 55,916 | 46,654 | 45 | 4,607 | 138,779 | 13,440 | 334,600 | 334,200 | 561,937 |
| Temp., °F. | 130 | 240 | 210 | 310 | 310 | 130 | 130 | 300 | 130 | 250 | 1,450 |
| Pressure, psia | 50 | 100 | 100 | 80 | 80 | 50 | 30 | 65 | 80 | 75 | 55 |

Examples of catalyst 12 are as follows:

A typical catalyst in 12 comprises iron oxide, chromium oxide and an alkali metal carbonate such as potassium carbonate. Another catalyst is stannic phosphate. In general the oxidative dehydrogenation process is well known in the art. For example, see U.S. Pat. Nos. 3,320,329 and 3,409,697.

Examples of catalyst 30 are as follows:

Catalysts that can be used in 30 are for example zinc aluminate preferably promoted by a small amount of metal active for initiating oxidative reactions. Such metals can be found in Groups IIIB, IVB, VB, VIB, VIIB, VIII, IB and VA of the periodic table.

Other modifications and alterations of this invention will become apparent to those skilled in the art from the foregoing discussion, examples and accompanying drawing, and it should be understood that this invention is not to be unduly limited thereto.

What is claimed is:

1. In an oxidative dehydrogenation process comprising passing a feed stream comprising heated air, steam, and hydrocarbons into a dehydrogenation catalytic reactor, catalytically converting the feed stream in the reactor, and discharging an effluent stream from the reactor for further processing, said reactor effluent comprising water, dehydrogenated hydrocarbon, oxygenated hydrocarbon derivatives, and unconverted hydrocarbon, the improvement comprising: continuously during said carrying out the steps of
   A. separating water from the dehydrogenation reactor effluent;
   B. passing the separated water into a catalytic oxidation reactor;
   C. treating said separated water in said catalytic oxidation reactor so as to convert any organic compounds therein to a carbonaceous gas; and thereafter
   D. passing the treated water from said catalytic oxidation reactor into the dehydrogenation catalytic reactor.

2. A process, as set forth in claim 1, wherein the carbonaceous gas comprises carbon monoxide and carbon dioxide.

3. A process, as set forth in claim 1, wherein the hydrocarbon feed stream to the dehydrogenation catalytic reactor comprises butenes and effluent from said reactor comprises butadiene.

4. A process, as set forth in claim 1, wherein the treated water effluent of the catalytic oxidation reactor is steam.

* * * * *

UNITED STATES PATENT AND TRADEMARK OFFICE
CERTIFICATE OF CORRECTION

PATENT NO. : 4,021,500
DATED : May 3, 1977
INVENTOR(S) : Ronald S. Rogers

It is certified that error appears in the above—identified patent and that said Letters Patent are hereby corrected as shown below:

In column 4, line 24 (claim 1), --- process --- should be inserted after "said".

Signed and Sealed this twenty-third Day of August 1977

[SEAL]

Attest:

RUTH C. MASON
Attesting Officer

C. MARSHALL DANN
Commissioner of Patents and Trademarks